(12) United States Patent
Greenawalt (10) Patent No.: US 6,510,626 B1
(45) Date of Patent: Jan. 28, 2003

(54) CUSTOM ORTHOTIC FOOT SUPPORT ASSEMBLY

(76) Inventor: Kent S. Greenawalt, 6935 Suncrest Dr., Roanoke, VA (US) 24014

( * ) Notice: Subject to any disclaimer, the term of this patent is extended or adjusted under 35 U.S.C. 154(b) by 0 days.

(21) Appl. No.: 09/628,155

(22) Filed: Jul. 28, 2000

(51) Int. Cl.⁷ .................. A43B 13/38; A43B 23/00; A61F 5/14
(52) U.S. Cl. .............. 36/43; 36/160; 36/166; 36/174; 36/178
(58) Field of Search .................. 36/43, 44, 28, 36/30 R, 31, 25 R, 313, 142, 143, 144, 145, 147, 154, 160, 166, 172, 173, 174, 178, 181

(56) References Cited

U.S. PATENT DOCUMENTS

| | | | | |
|---|---|---|---|---|
| 2,862,313 A | * | 12/1958 | Jones | 36/145 |
| 4,215,492 A | * | 8/1980 | Sandmeier | 36/44 |
| 4,486,964 A | * | 12/1984 | Rudy | 36/28 |
| 4,628,936 A | * | 12/1986 | Langer et al. | 36/43 |
| 4,694,590 A | | 9/1987 | Greenawalt | |
| 4,783,910 A | * | 11/1988 | Boys, II et al. | 36/30 R |
| 4,794,707 A | * | 1/1989 | Franklin et al. | 36/30 R |
| 4,841,648 A | * | 6/1989 | Shaffer et al. | 36/145 |
| 5,493,792 A | * | 2/1996 | Bates et al. | 36/28 |
| 5,787,608 A | | 8/1998 | Greenawalt | |
| 5,832,634 A | * | 11/1998 | Wong | 36/30 R |
| 5,976,100 A | | 11/1999 | Greenawalt | |
| 6,038,790 A | * | 3/2000 | Pyle et al. | 36/30 R |
| 6,048,810 A | * | 4/2000 | Baychar | 36/44 |
| 6,082,023 A | * | 7/2000 | Dalton | 36/28 |
| 6,176,025 B1 | * | 1/2001 | Patterson et al. | 36/28 |

FOREIGN PATENT DOCUMENTS

| | | | | |
|---|---|---|---|---|
| EP | 154737 | * | 9/1985 | 36/145 |
| GB | 2244200 | * | 11/1991 | 36/3 B |

* cited by examiner

*Primary Examiner*—Anthony D. Stashick
(74) *Attorney, Agent, or Firm*—Henderson & Sturm LLP (57) ABSTRACT

An orthotic foot support construction having a sole, an orthotic unit for a foot of the wearer, a propulsion component adhered to the sole and located to provide upward propulsion of the forefoot of the foot support wearer in response to forefoot pressure on the component, and a covering for cooperating with the sole to provide a unitary construction. The orthotic foot support construction may be custom-made with the orthotic unit especially prescribed.

2 Claims, 5 Drawing Sheets

CUSTOM ORTHOTIC FOOT SUPPORT ASSEMBLY

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates generally to footwear and specifically to custom-made footwear incorporating orthotics and foot orthotics.

2. Background Art

In the cycle of normal walking, there are two phases, a stance phase and a swing phase. The stance phase occurs when a person is standing on their feet, and the swing phase is when the person brings his/her leg forward to take another step, etc. The stance phase is in three parts—the initial heel contact, the full plantar, and thirdly the propulsion, sending the walker forward.

The use of custom made orthotics—inserts for shoes; orthopedic shoes for helping certain foot problems; shoe modifications in the form of heel built-ups; and rocker-type bottoms for shoes; and custom sandals, as examples of solving certain orthopedic problems are well known in this field. Applicant has personally developed and manufactured custom-made orthotics in this field as shown in U.S. Pat. Nos. 5,787,608 and 5,976,100.

However, to applicant's knowledge, no one has addressed the total problem of enhancing the stance phase of personal walking in the specialized field of custom-made orthotic foot support constructions, and in orthotics, sandals, clogs and/or shoes.

DISCLOSURE OF THE INVENTION

The present invention relates to a custom-made orthotic support assembly which comprises specific orthotic elements, and a propulsion component designed specifically to enhance the propulsion part of the gait cycle of a person during the stance phase, this orthotic support assembly adapted for insertion into or as an integral part of contemporary footwear, including but not limited to all forms of shoes, sandals, clogs and the like.

More particularly, the invention comprises a sole having an outline in plan of the foot of the wearer, with a heel portion and a forward portion; a prescribed orthotic unit which may include a plurality of orthotic elements such as arch and heel supports; a propulsion component specifically placed on the forward portion of the sole so as to receive the full plantar of the wearer during the stance phase of the gait cycle; and a covering unit for the orthotic elements and propulsion component whereby to form with the sole a unitary custom-made foot support.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Referring now to FIGS. 1–4, the embodiment of the invention depicted includes a custom-made orthotic foot support assembly (10) for placement into or on to any type of footwear or as an integral part thereof, and comprises generally a sole (12) of a thin layer of leather or the like having an outline of the foot of the wearer so as to support the entire foot, and of a thickness as predetermined for its use, the sole (12) having a heel portion (14) and a portion (16) forward of the heel portion (14).

The assembly (10) comprises further an orthotic unit (18) adhered to the sole (12) and prescribed to the wearer's foot, and comprises further a propulsion component (20) placed on and adhered to the forward portion (16) of the sole (12). A covering unit (22) cooperates with the sole (12), the orthotic unit (18) and the propulsion component (20) to form the unitary foot support (10).

Figure 1:
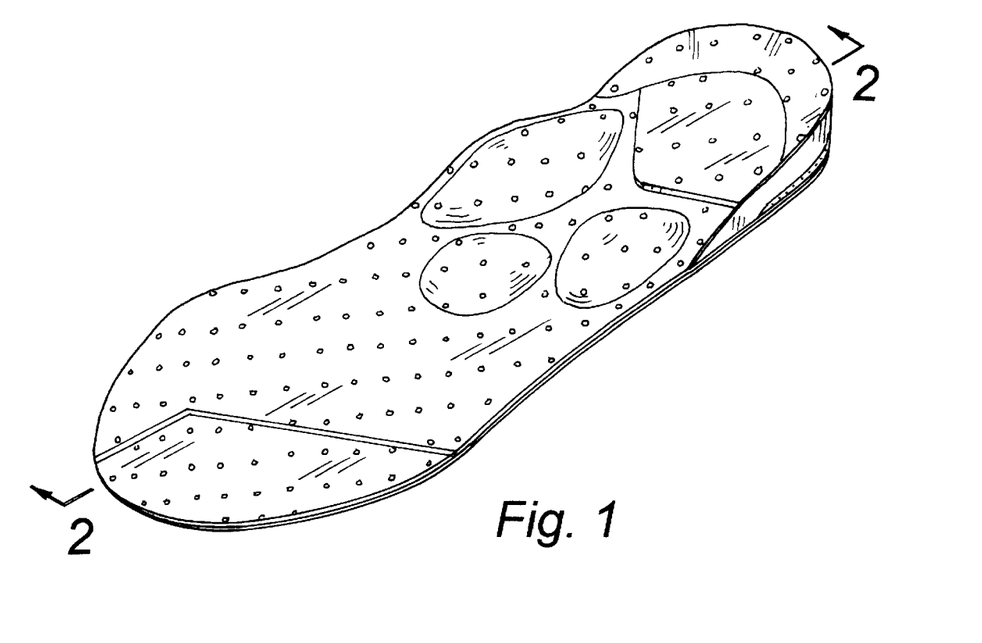
FIG. 1 comprises a perspective view of the custom made orthotic foot support assembly of this invention.
Figure 2:
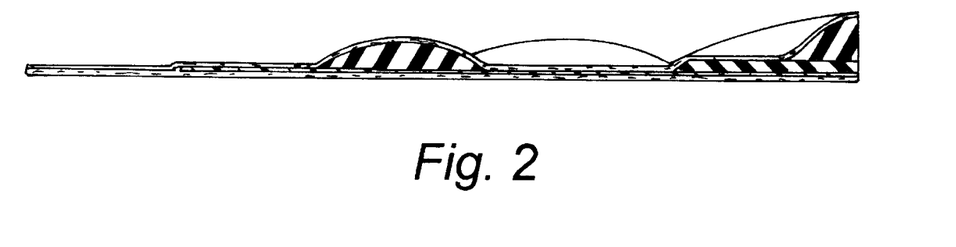
FIG. 2 is a vertical sectional view taken along the line 2—2 of FIG. 1.
Figure 3:
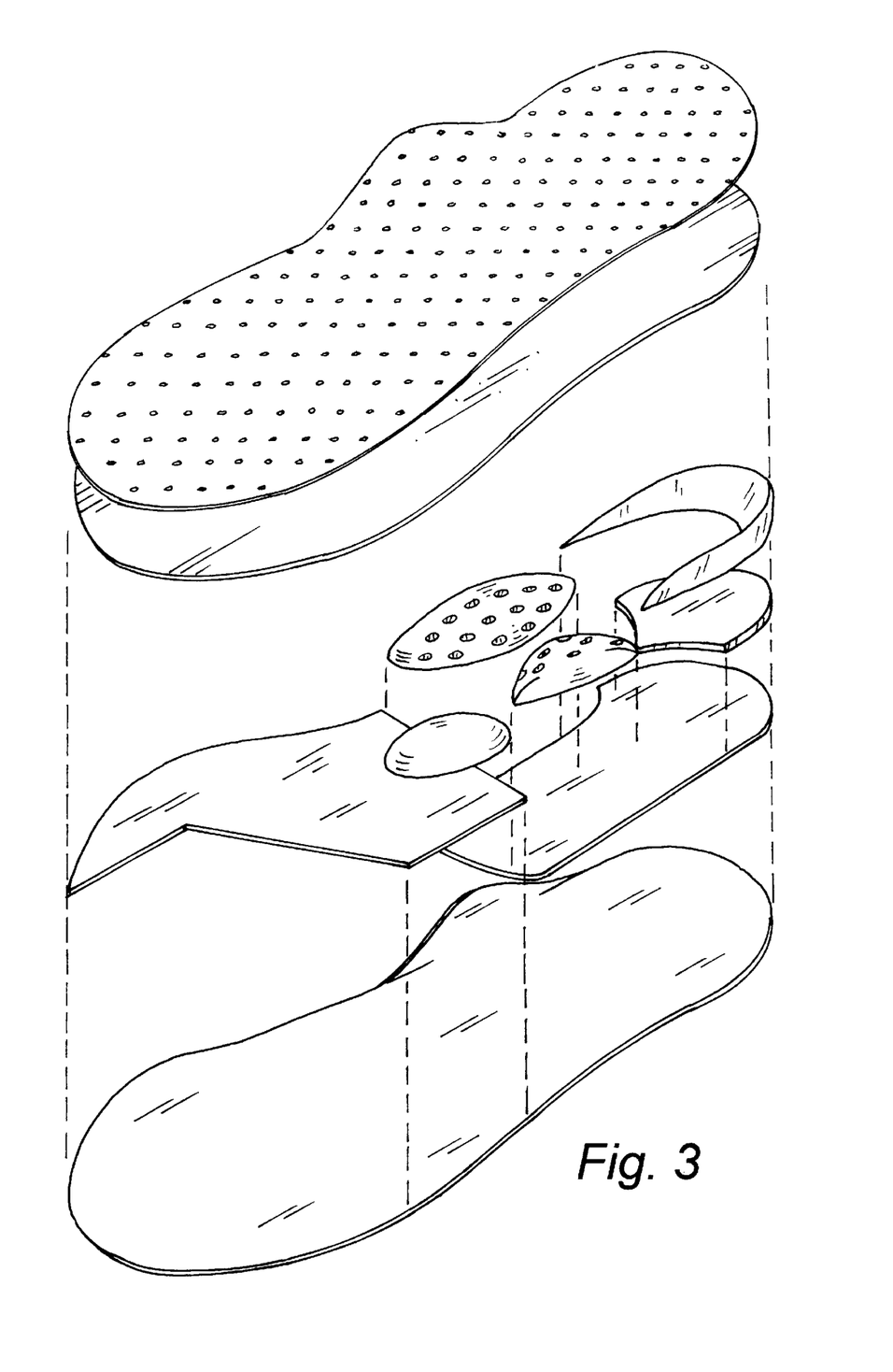
FIG. 3 is an exploded view in perspective of the orthotic foot support assembly of FIG. 1.
Figure 4:
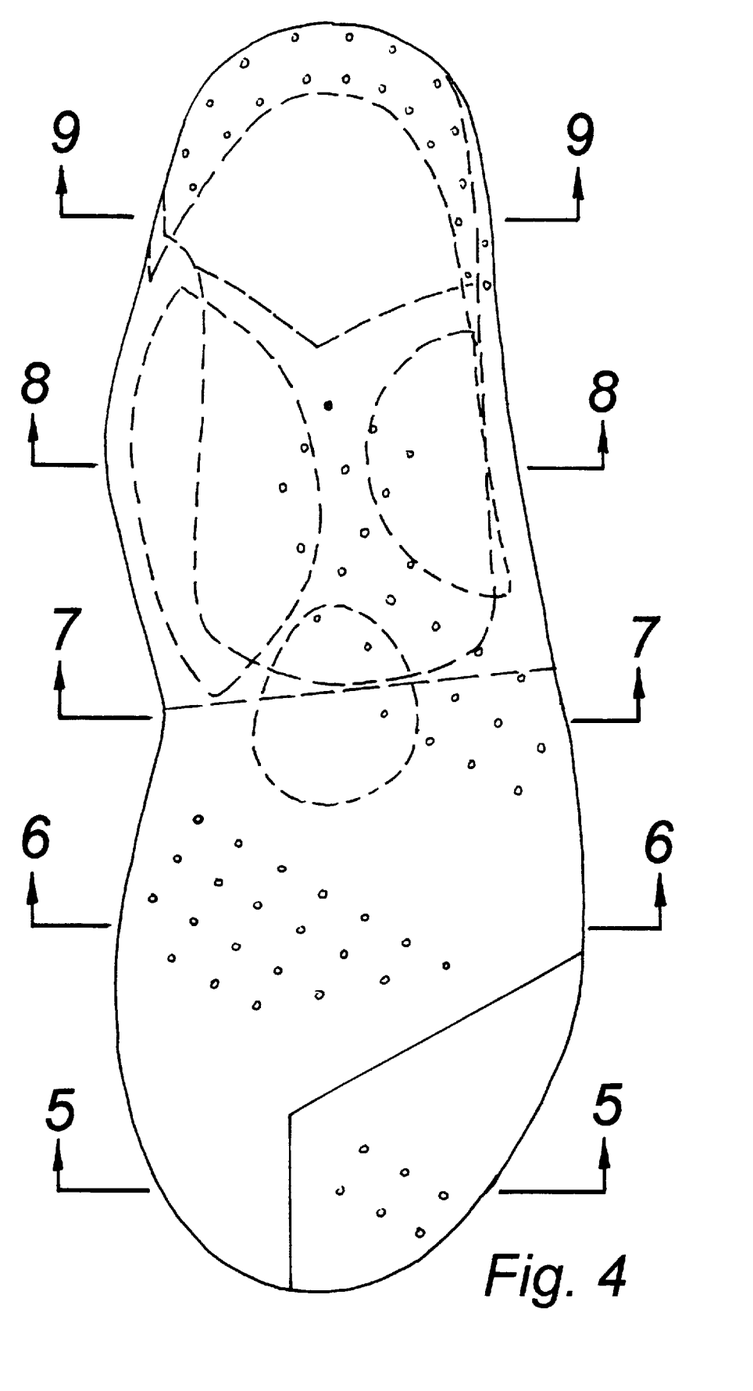
FIG. 4 is a plan view of the assembly of FIG. 1.

More particularly, the orthotic unit (18) includes a lower, semi-flexible thin element (24) of fiber board-type material and having generally an outline similar to that of the heel portion (14) of the sole (12) and adhered thereover in a mating relationship as best seen in FIG. 4; a heel inset (26) of a polyurethane foam providing a high degree of shock absorption, and of a curved shape and thin thickness to fit over and be adhered to the rear portion (28) of the lower element (24) (FIG. 4), so as to mate therewith. Sponge rubber-type arch support elements (30), (32), (34) (FIG. 3) formed according to prescribed arch support needs of the individual for whom the support assembly (10) is custom made, are adhered to the upper surfaces of the lower element (24) and the propulsion component (20) (FIG. 3) at prescribed locations. The arch support elements (32) and (34) may be perforated for special requirements.

A cup-shaped counter (35) of any type of resilient shock absorbing supportive material of a certain density, formed to fit over and be adhered to the rear, semi-circular portion of the heel insert (26) and possibly peripheral portions of the lower element (24) is also provided.

Preparation of the orthotic unit (18) may comprise use by a chiropractor, or other health care person skilled in this field and licensed to prescribe orthotics, of a casting kit as described in U.S. Pat. No. 3,320,347 entitled Method of Making an Arch Support by Measuring an Impression of a Foot, issued May 16, 1967 to M. H. Greenawalt, which patent is incorporated herein by reference. Preparation of the orthotic unit (18) may also comprise the use of an electronic casting machine that is capable of sending three dimensional data of the foot to the laboratory for manufacturing purposes. The results of the casting or foot impression mold are then analyzed and a prescription is generated. Other methods of preparation may be utilized, and the invention is not to be limited thereby. These elements (30)–(34) support the three arches of the foot: the inner-longitudinal arch (navicular), the outer-longitudinal arch (cuboid), and the anterior transverse arch. The heel inset (26) is placed into the heel zone of the orthotic unit (18) to absorb shock during the first phase (heel strike) of the gait cycle. Rear foot posting for pronation or supination is built into the orthotic design to achieve proper foot posture and balance. Heel spur accommodations as well as a heel lift for an anatomical short leg can be built into the orthotic based on the individual's specific needs.

Figure 6:
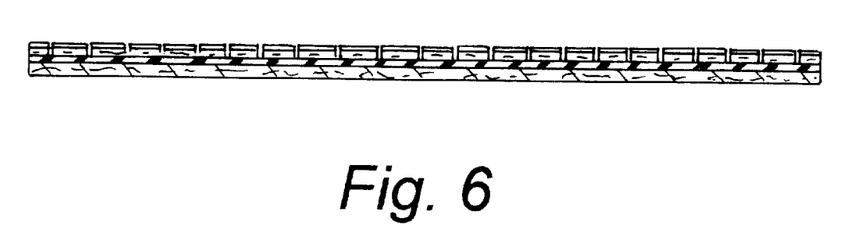
Figures 6, 7:
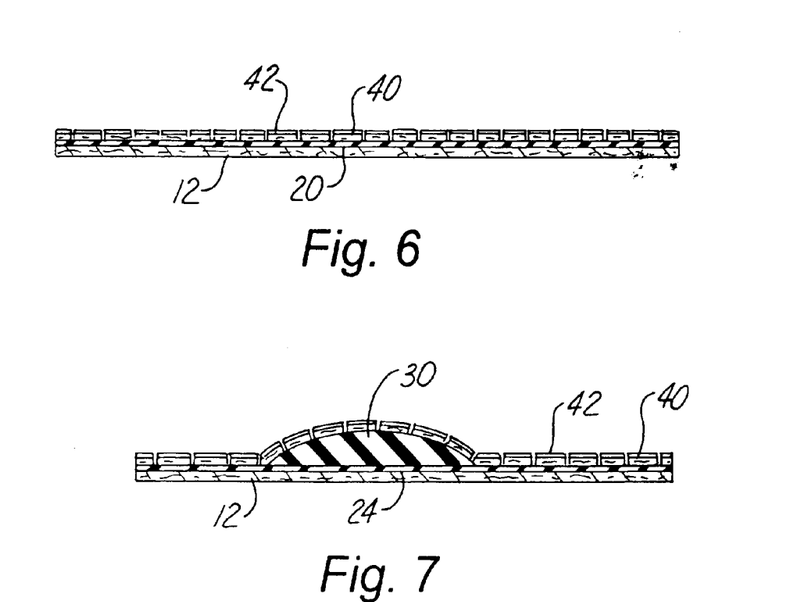
Figure 7:
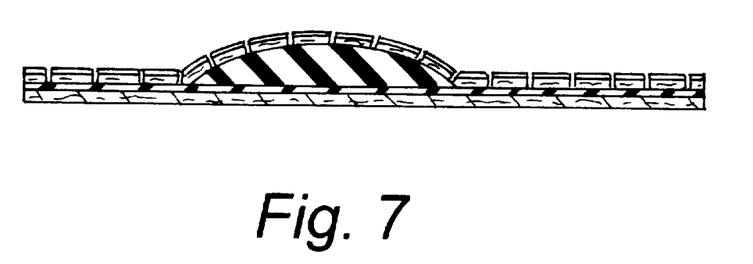
Figure 8:
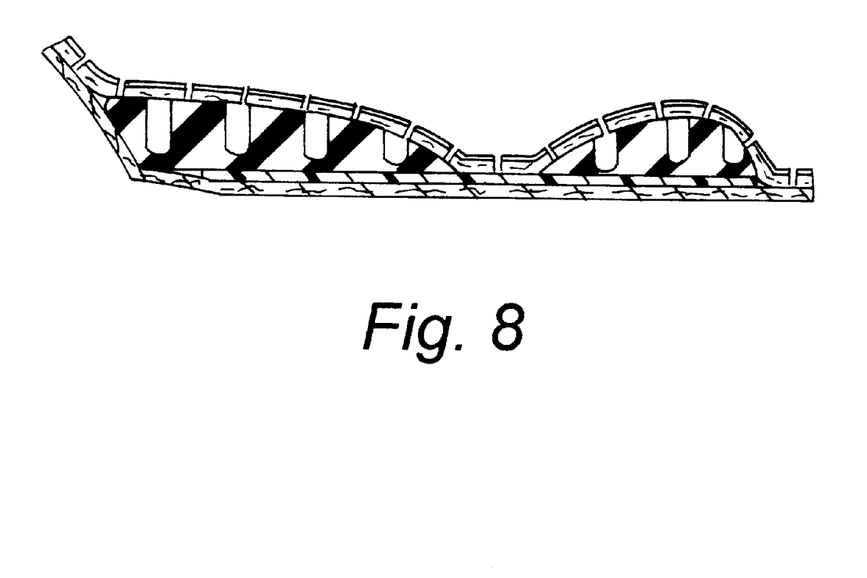
Figure 9:
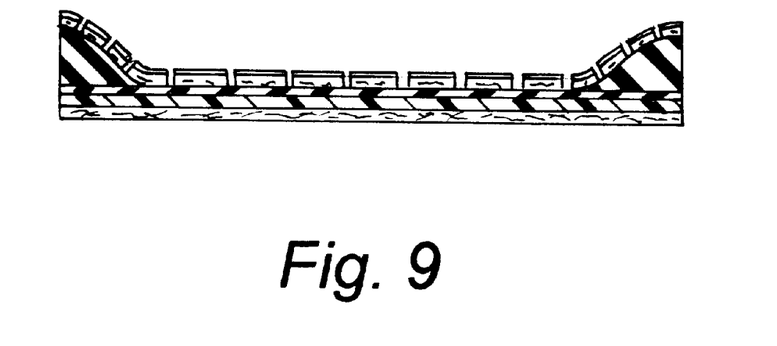

The propulsion component (20) is a micro-cellular polyurethane material that retains its shape, thickness and resiliency for at least the life of the orthotic foot support assembly (10). It is breathable and has a high vapor transmission quality. Referring to FIGS. 3, 4 and 6, it is seen to have a thickness comparable to or less than the sole (12), with a shape and outline similar to that of the sole (12) at the forward portion (16) thereof, except for a cutout portion indicated by the edges (36), (38) (FIG. 3) which may be provided. Material other than the micro-cellular polyurethane of the component (20) may be utilized, the only requirement being that it have a comparable rebounding characteristic.

In the context of the conventional gait cycle of a person, consisting of a stance phase and a swing phase, the latter when a leg is moving forward, the stance phase is broken down into three parts, the initial heel part or strike, the full planar of the foot, or midstance, and the propulsion part, or "toe off." The present invention provides a custom-made orthotic foot support assembly (10) which provides the heel insert (26), and counter (35) as a heel pad for absorbing the heel strike shock; the midstance variable firmness and flexibility provided by the lower element (24) and the arch supports (30)–(34); and now a boost or propulsion component (20) for the "toe off" propulsion part of the stance phase. Thus, the assembly (10) provides a comprehensive structure for the shock absorption, corrective support and propulsive "boost" for complete support and comfort throughout the entire gait cycle.

Figure 5:
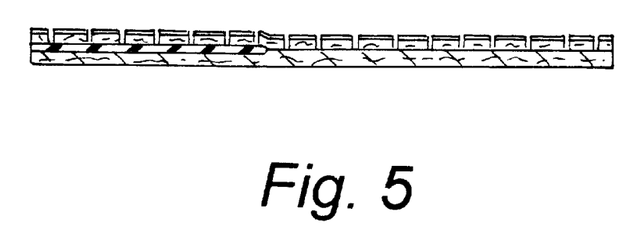
FIGS. 5–9 are fragmentary, vertical sectional views taken along their respective lines of FIG. 4.

The covering unit (22) includes a thin layered pad (40) (FIG. 5) of polyurethane and a thinner layer (42) of leather or the like disposed above the pad (40). Both pad (40) and layer (42) have an outline similar to that of the sole (12), with the pad (40) and layer (42) bonded together and adhered in any conventional manner with the remaining elements to form the unitary foot support assembly (10). Further, both pad (40) and layer (42) may be perforated, as desired.

Thus, from this description, it may readily be seen that the custom made orthotic foot support assembly (10) of this invention provides not only the corrective support of orthotics, but also the support and comfort for the entire gait cycle, and more particularly the propulsion part of the stance part thereof.

What is claimed is:

1. A footwear construction custom-made for a wearer having a foot with a front of the foot and a heel at the rear of the foot, comprising:
   a sole having a forward portion and a heel portion integrally joined and of a substantially constant thickness;
   an orthotic unit prescribed specially for a foot of the wearer, and adhered to said sole;
   means responsive to pressure thereon of the front of the foot comprising a component adhered in its entirety to the said forward portion of said sole, said component having an outline similar to the outline of the said forward portion of said sole, and located on said sole to receive only the front of the foot, said component is resilient and flexible and comprised of a micro-cellular polyurethane material and provides an upward propulsion of the front of the wearer's foot upon movement of the front of the foot away from said orthotic unit;
   a covering unit for said orthotic unit and said resilient component, said covering unit including a thin-layered resilient pad and a thinner layer of leather, both pad and layer perforated for aeration of said orthotic unit; and
   further wherein said orthotic unit includes a heel pad insert adhered to said heel portion for absorbing heel strike shock as the wearer comes down on the heel of a foot and includes further arch support elements specially prescribed and adhered to said sole for midstance support of the wearer's foot.

2. A footwear construction custom-made for a wearer having a front of the foot and a heel at the rear of the foot, comprising:
   a sole having a forward portion and a heel portion rearward of said forward portion, said forward portion and said heel portion integrally joined and having a substantially constant thickness;
   an orthotic unit prescribed specially for a foot of the wearer, said orthotic unit including a heel inset of a curved shape and thin thickness fit over and adhered to said heel portion so as to mate therewith, said heel inset providing a high degree of shock absorption in response to the load applied thereto by the wearer's heel;
   a semi-flexible thin member adhered to said heel portion of said sole, in a mating relationship, said member having an outline in plan generally similar to said sole heel portion;
   said orthotic unit including additionally a plurality of sponge rubber arch support elements formed according to prescribed arch support needs of the wearer, said elements adhered to the said member, said orthotic unit providing midstance firmness, flexibility and corrective support;
   a propulsion component of a material that retains its shape, thickness and resiliency during use for providing a rebounding characteristic, said component having a shape similar to said sole at said forward portion and adhered thereto, said component having a thickness comparable to said sole, said propulsion component, being breathable and having a high vapor transmission quality, and providing a boost to the tee-off step of the wearer; and
   a unit for covering said orthotic unit and said propulsion component, and adhered to said sole.

* * * * *

UNITED STATES PATENT AND TRADEMARK OFFICE
CERTIFICATE OF CORRECTION

PATENT NO.     : 6,510,626 B1
DATED          : January 28, 2003
INVENTOR(S)    : Kent S. Greenawalt It is certified that error appears in the above-identified patent and that said Letters Patent is hereby corrected as shown below:

In the title page, the drawing is incorrect. The reference numerals were omitted.

Drawings,
Sheets 1-5, Figs. 1, 2, 3, 4, 5, 6, 7, 8 and 9, the reference numerals have been omitted. Please insert the attached drawing sheets of Figs. 1,2,3,4,5,6,7,8 and 9 showing the reference numerals.

Signed and Sealed this

Twelfth Day of October, 2004

JON W. DUDAS
*Director of the United States Patent and Trademark Office*

(12) United States Patent
Greenawalt (10) Patent No.: US 6,510,626 B1
(45) Date of Patent: Jan. 28, 2003

(54) CUSTOM ORTHOTIC FOOT SUPPORT ASSEMBLY

(76) Inventor: Kent S. Greenawalt, 6935 Suncrest Dr., Roanoke, VA (US) 24014

(*) Notice: Subject to any disclaimer, the term of this patent is extended or adjusted under 35 U.S.C. 154(b) by 0 days.

(21) Appl. No.: 09/628,155

(22) Filed: Jul. 28, 2000

(51) Int. Cl.⁷ .................. A43B 13/38; A43B 23/00; A61F 5/14

(52) U.S. Cl. .................. 36/43; 36/160; 36/166; 36/174; 36/178

(58) Field of Search .................. 36/43, 44, 28, 36/30 R, 31, 25 R, 313, 142, 143, 144, 145, 147, 154, 160, 166, 172, 173, 174, 178, 181

(56) References Cited

U.S. PATENT DOCUMENTS

| | | | |
|---|---|---|---|
| 2,862,313 A | * 12/1958 | Jones | 36/145 |
| 4,215,492 A | * 8/1980 | Sandmeier | 36/44 |
| 4,486,964 A | * 12/1984 | Rudy | 36/28 |
| 4,628,936 A | * 12/1986 | Langer et al. | 36/43 |
| 4,694,590 A | 9/1987 | Greenawalt | |
| 4,783,910 A | * 11/1988 | Boys, II et al. | 36/30 R |
| 4,794,707 A | * 1/1989 | Franklin et al. | 36/30 R |
| 4,841,648 A | * 6/1989 | Shaffer et al. | 36/145 |
| 5,493,792 A | * 2/1996 | Bates et al. | 36/28 |
| 5,787,608 A | 8/1998 | Greenawalt | |
| 5,832,634 A | * 11/1998 | Wong | 36/30 R |
| 5,976,100 A | 11/1999 | Greenawalt | |
| 6,038,790 A | * 3/2000 | Pyle et al. | 36/30 R |
| 6,048,810 A | * 4/2000 | Baychar | 36/44 |
| 6,082,023 A | * 7/2000 | Dalton | 36/28 |
| 6,176,025 B1 | * 1/2001 | Patterson et al. | 36/28 |

FOREIGN PATENT DOCUMENTS

| | | | | |
|---|---|---|---|---|
| EP | 154737 | * 9/1985 | | 36/145 |
| GB | 2244200 | * 11/1991 | | 36/3 B |

* cited by examiner

Primary Examiner—Anthony D. Stashick
(74) Attorney, Agent, or Firm—Henderson & Sturm LLP (57) ABSTRACT

An orthotic foot support construction having a sole, an orthotic unit for a foot of the wearer, a propulsion component adhered to the sole and located to provide upward propulsion of the forefoot of the foot support wearer in response to forefoot pressure on the component, and a covering for cooperating with the sole to provide a unitary construction. The orthotic foot support construction may be custom-made with the orthotic unit especially prescribed.

2 Claims, 5 Drawing Sheets